United States Patent
Crescimanno et al.

(10) Patent No.: US 11,445,794 B2
(45) Date of Patent: Sep. 20, 2022

(54) METHODS AND COMPOSITIONS FOR READILY REMOVING NAIL COATINGS

(71) Applicant: Mycone Dental Supply Company, Inc., Gibbstown, NJ (US)

(72) Inventors: Stephen Crescimanno, Hatfield, PA (US); Paul L. Fishbein, Cherry Hill, NJ (US); Larry W. Steffier, Cherry Hill, NJ (US); Serene Y. Curry, Richboro, PA (US)

(73) Assignee: Mycone Dental Supply Company, Inc., Gibbstown, NJ (US)

( * ) Notice: Subject to any disclaimer, the term of this patent is extended or adjusted under 35 U.S.C. 154(b) by 430 days.

(21) Appl. No.: 16/064,631

(22) PCT Filed: Dec. 21, 2016

(86) PCT No.: PCT/US2016/067989
§ 371 (c)(1),
(2) Date: Jun. 21, 2018

(87) PCT Pub. No.: WO2017/112754
PCT Pub. Date: Jun. 29, 2017

(65) Prior Publication Data
US 2019/0000208 A1    Jan. 3, 2019

Related U.S. Application Data

(63) Continuation of application No. 14/978,806, filed on Dec. 22, 2015, now abandoned.

(51) Int. Cl.
| | | |
|---|---|---|
| *A45D 29/00* | (2006.01) | |
| *A45D 29/18* | (2006.01) | |
| *A61K 8/81* | (2006.01) | |
| *A45D 34/04* | (2006.01) | |
| *A61K 8/04* | (2006.01) | |
| *A61Q 3/02* | (2006.01) | |
| *A61Q 3/00* | (2006.01) | |
| *A61K 8/891* | (2006.01) | |

(52) U.S. Cl.
CPC ........... *A45D 29/007* (2013.01); *A45D 29/00* (2013.01); *A45D 29/18* (2013.01); *A45D 34/042* (2013.01); *A61K 8/042* (2013.01); *A61K 8/8111* (2013.01); *A61K 8/8117* (2013.01); *A61K 8/8135* (2013.01); *A61K 8/8152* (2013.01); *A61K 8/891* (2013.01); *A61Q 3/00* (2013.01); *A61Q 3/02* (2013.01); *A61K 2800/87* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | |
|---|---|---|
| 3,390,206 A | 6/1968 | Thompson et al. |
| 5,921,250 A | 7/1999 | Rhea et al. |
| 6,224,887 B1 | 5/2001 | Samour et al. |
| 6,803,394 B2 | 10/2004 | Lilley et al. |
| 8,697,619 B2 | 4/2014 | Steffier et al. |
| 2006/0016455 A1 | 1/2006 | Ide |
| 2010/0178321 A1 | 7/2010 | Hanatani et al. |
| 2013/0263875 A1 | 10/2013 | Burgess et al. |
| 2013/0319441 A1 | 12/2013 | Ma |
| 2015/0265524 A1 | 9/2015 | Li et al. |
| 2015/0313831 A1 | 11/2015 | Li et al. |
| 2016/0030310 A1 | 2/2016 | Kozacheck et al. |
| 2016/0175212 A1 * | 6/2016 | Zhou .................. A61K 8/8152 424/61 |

FOREIGN PATENT DOCUMENTS

| | | | |
|---|---|---|---|
| CN | 101600744 | 12/2009 | |
| CN | 102597130 | 7/2012 | |
| CN | 102658222 | 8/2012 | |
| CN | 105816348 | 8/2016 | |
| JP | S5528930 | 2/1980 | |
| JP | S59226077 | 12/1984 | |
| JP | S6148369 | 3/1986 | |
| JP | H0770519 | 3/1995 | |
| JP | H093104 | 1/1997 | |
| JP | 2011229725 | 11/2011 | |
| JP | 2015188465 | 11/2015 | |
| KR | 101529461 | 6/2015 | |
| WO | WO-0143579 A1 * | 6/2001 | ............. A45D 29/00 |
| WO | WO 2012/147613 | 11/2012 | |
| WO | 2014/086862 | 6/2014 | |
| WO | 2014/152964 | 9/2014 | |
| WO | WO-2014135659 A2 * | 9/2014 | ............... A61K 8/87 |

OTHER PUBLICATIONS

SAAPedia Polyacrylate-21 < http://www.saapedia.org/en/saa/?type=detail&id=4715> accessed Feb. 26, 2021; available Sep. 8, 2014 (Year: 2014).*
English translation of WO-2014135659-A2 (Year: 2014).*
International Search Report and Written Opinion in International Application No. PCT/US2016/067989, dated Mar. 2, 2017, 16 pages.
Pyun, J. et al. "Synthesis of Polymer Brushes Using Atom Transfer Radical Polymerization" Macromolecular Rapid Communications, 2003, 24(18), 1043-1059.
Extended European Search Report in European Application No. 16880017, dated Jul. 26, 2019, 7 pages.

* cited by examiner

*Primary Examiner* — Nicole P Babson
(74) *Attorney, Agent, or Firm* — Fish & Richardson P.C.

(57) ABSTRACT

A method and kit for treating a nail surface. The method includes brushing or spraying an adhesive on a coated or uncoated nail surface to form an adhesive-coated surface. A covering (e.g., a curable nail gel, evaporative nail polish, or artificial nail) is then applied to the adhesive-coated surface. The covering is removable by soaking in solvent for less than 20 minutes, peeling, or a combination thereof.

20 Claims, No Drawings

METHODS AND COMPOSITIONS FOR READILY REMOVING NAIL COATINGS

CROSS-REFERENCE TO RELATED APPLICATIONS

This application is a National Stage Application under 35 U.S.C. § 371 and claims the benefit of International Application No. PCT/US2016/067989, filed Dec. 21, 2016, which claims priority to U.S. application Ser. No. 14/978,806, filed Dec. 22, 2015. The disclosures of the foregoing applications are hereby incorporated by reference in their entirety.

TECHNICAL FIELD

This invention relates to removing nail coatings, e.g., curable gel coatings or evaporative polishes, from coated and uncoated nail surfaces.

BACKGROUND

Both evaporative nail polishes and curable gel coatings have been used to coat natural and artificial nails, including nail extensions. The evaporative polishes can be water-borne or in the form of a solution with an organic solvent. Following application, the coating is dried to remove solvent. Drying times can be as long as an hour or more, depending on the number of coats applied. The dried coating is typically treated with a solvent such as acetone when it is desired to change or remove the polish.

The gel compositions typically include acrylic or methacrylic monomers and oligomers. Once cured following application, e.g., by exposure to ultraviolet or visible radiation, or by thermal or redox methods, the gels form a hard, durable coating in a relatively short period of time on the order of minutes. Removing the cured coating, however, is more difficult than removing an evaporative polish. Typically it is necessary to soak the coated nail with solvent such as acetone, ethyl acetate, amyl acetate, ethanol, butanol, or the like for a period of time, with the aid of a cotton ball or nail wipe covered with foil, or by soaking in a bowl of solvent, after which the cured gel coating is removed.

SUMMARY

In one aspect, there is described a method for treating a nail surface that includes brushing or spraying an adhesive on a coated or uncoated nail surface to form an adhesive-coated surface. For example, the adhesive may be applied by dipping a brush in a container holding the adhesive and then using the brush to spread the adhesive on the nail surface. Alternatively, the adhesive may be squeezed onto the nail surface and then manipulated, e.g., using a brush so that it covers the desired area of the nail surface. A covering (e.g., a curable nail gel, evaporative nail polish, or artificial nail) is then applied to the adhesive-coated surface. The covering is removable by soaking in solvent for less than 20 minutes, peeling, or a combination thereof.

The adhesive may be applied to the entire nail surface or to a portion of the nail surface. In some embodiments, the covering is removable by soaking in solvent for less than 20 minutes or less than 10 minutes. In other embodiments, the coating is removable by peeling it from the adhesive.

The adhesive may be a solvent-based or aqueous-based adhesive. In some embodiments, it is formed in situ following application to the nail surface. Examples of suitable adhesives include (meth)acrylates, silicones, polyvinyl acetates, polyethylene vinyl acetates, polyisoprene rubbers, styrene-methacrylate copolymers, styrene-butadiene rubbers, methacrylate-butadiene-styrene copolymers, and combinations thereof. Branched polymers such as comb and star polymers are additional examples of suitable adhesives that may be used. The branched polymers may, in some embodiments, include reactive groups in the polymer chain.

In one embodiment, the adhesive is a crosslinked (meth)acrylate copolymer. An example of such an adhesive is the polymerization product of (a) a $C_1$-$C_{20}$ alkyl methacrylate monomer (e.g., butyl methacrylate); (b) a $C_1$-$C_{20}$ alkyl acrylate monomer (e.g., butyl acrylate), and (c) an ethylenically unsaturated (meth)acrylate crosslinking monomer (e.g., an alkylene glycol dimethacrylate). Uncrosslinked adhesives may be used as well. The adhesive may also include mixtures of different types of adhesives. For example, in some embodiments, e.g., for use with artificial nails or nail tips, the adhesive may be blended with, e.g., a cyanoacrylate adhesive to assist in adhering the artificial nail or nail tip to the underlying nail surface. The amount of the second adhesive is selected such that it does not compromise removability.

The nail covering may be a curable gel coating (e.g., a base coat, color coat, or top coat), an evaporative nail polish, a reactive nail polish, an artificial nail or nail tip, or nail art. The artificial nail or nail tip, in turn, may be adhered to the adhesive-coated surface via a second adhesive such as a cyanoacrylate adhesive. The nail covering may be in the form of a continuous coating. Alternatively, it may be discontinuous. An example of the latter is a decal or decorative design.

In some embodiments, the adhesive is applied to an uncoated nail surface. In other embodiments, the nail surface is a coated nail surface. For example, the nail surface may be coated with a cured nail gel (e.g., a base coat or color coat).

Also described is a kit that includes (a) a brushable or sprayable adhesive suitable for application to a coated or uncoated nail surface; and (b) a nail covering selected from the group consisting of radiation-curable nail gels, evaporative nail polishes, artificial nails, and combinations thereof. When the adhesive is applied to a coated or uncoated nail surface, followed by application of the nail covering, the nail covering is removable by soaking in solvent for less than 20 minutes, peeling, or a combination thereof.

In another aspect, the nail covering may be combined with the adhesive. Accordingly, there is described a method for treating a nail surface that includes (a) providing a composition comprising (i) an adhesive and (ii) a nail covering selected from the group consisting curable gels, evaporative nail polishes, reactive nail polishes, and combinations thereof; and (b) applying the composition to a coated or uncoated nail surface by brushing or spraying. Following application, the nail covering is removable by soaking in solvent for less than 20 minutes, peeling, or a combination thereof.

The adhesive or adhesive/nail covering combination composition is applied to both coated and uncoated nail surfaces by simply brushing or spraying it on the surface. Therefore, it is easy for nail technicians for apply, unlike adhesive films, which must be positioned at a particular location on the nail surface. When it is desired to remove the nail covering, e.g., to change the color or type of covering, the covering is easily removed from the adhesive-coated surface by soaking for a limited amount of time or by simply peeling it off. Because the covering is easily removed, damage to the underlying nail surface is minimized.

The details of one or more embodiments of the invention are set forth in the description below. Other features, objects, and advantages of the invention will be apparent from the description and from the claims.

DETAILED DESCRIPTION

A solvent-based adhesive is brushed or sprayed on a coated or uncoated nail surface. The adhesive may be pre-polymerized. Alternatively, the adhesive may be polymerized in situ following application to the coated or uncoated nail surface. Once dried, the adhesive forms a tacky surface to which a nail covering may be adhered. Alternatively, the nail covering (gel coating, evaporative nail polish, reactive nail polish, or combination thereof) may be combined with the adhesive and the resulting composition applied to the coated or uncoated nail surface. The use of the adhesive makes it possible to remove the nail covering simply by peeling or by soaking for a relatively short period of time without damaging the underlying nail. In particular, when the nail covering is soaked off according to the protocol described in U.S. Pat. No. 6,803,394, which is incorporated by reference, using a soak-off agent selected from the group consisting of acetone, ethyl acetate, amyl acetate, ethanol, and butanol, the nail covering soaks off in 20 minutes or less.

In some embodiments, the adhesives are lightly crosslinked and engineered such that they fail cohesively when the nail covering is peeled off. This results in some adhesive remaining on the nail surface, which protects the nail surface from damage. Suitable adhesives include (meth)acrylates, silicones, polyvinyl acetates, polyethylene vinyl acetates, polyisoprene rubbers, styrene-methacrylate copolymers, styrene-butadiene rubbers, methacrylate-butadiene-styrene copolymers, and combinations thereof. In other embodiments, the adhesives are designed to fail adhesively.

Crosslinked (meth)acrylate copolymers have been found to be particularly useful. An example of such an adhesive is the polymerization product of (a) a $C_1$-$C_{20}$ alkyl methacrylate monomer; (b) a $C_1$-$C_{20}$ alkyl acrylate monomer, and (c) an ethylenically unsaturated (meth)acrylate crosslinking monomer (e.g., an alkylene glycol dimethacrylate). In some embodiments, the adhesive may also incorporate acrylic acid to improve cohesive strength.

Examples of suitable (meth)acrylate monomer include 2-hydroxyethyl (meth)acrylate/succinate adduct, acetoacetoxy (meth)acrylate, acetoacetoxy ethyl (meth)acrylate (AAEMA, AAEA), butyl (meth)acrylate, cyclohexyl (meth)acrylate, ethyl (meth)acrylate (EMA, EA), glycidyl (meth)acrylates, hexyl (meth)acrylate, hydroxyethyl (meth)acrylate (HEMA, HEA), hydroxyethyl (meth)acrylate acetate, hydroxypropyl (meth)acrylate (HPMA, HPA), isobutyl (meth)acrylate, lauryl (meth)acrylate, maleic anhydride, methoxy polyethylene glycol (350) mono(meth)acrylate, mono or poly (meth)acrylic acids, phthalic acid monoethyl (meth)acrylate, polybutylene glycol (meth)acrylates, polyethylene glycol (600) mono(meth)acrylate, polyethylene glycol (meth)acrylates, polypropylene glycol (meth)acrylates, PPG mono(meth)acrylate, stearyl (meth)acrylate, tetrahydrofurfuryl (meth)acrylate (THFMA, THFA), tridecyl (meth)acrylate, and urethane (meth)acrylate.

Examples of suitable crosslinking monomers include 1,3-glycerol di(meth)acrylate/succinate adduct, 2-hydroxyethyl di(meth)acrylate/succinate adduct, ethylene glycol di(meth)acrylate, glycidyl (meth)acrylate, isopropylidenediphenyl bisglycidyl (meth)acrylate, methacroyloxyethyl maleate, neopentylglycol di(meth)acrylate, organosilanes, organotitanates, PEG-4 di(meth)acrylate, propoxylated allyl (meth)acrylate, pyromellitic di(meth)acrylate, pyromellitic dianhydride di(meth)acrylate, pyromellitic dianhydride glyceryl di(meth)acrylate (PMGDM, PMGD), tetraethylene glycol di(meth)acrylate, triethylene glycol di(meth)acrylate, and trimethlolpropane tri(meth)acrylate.

Branched polymers with a more controlled structure broadly referred to as comb or star polymers may also be used as the adhesive. Comb polymers are a class of branched polymers where two or more polymer branches of a defined composition and Molecular Weight (MW) are covalently attached to a main polymer backbone. Star polymers or dendrimers are a subset of comb polymers where the main polymer backbone is small (i.e., oligomeric or monomeric) relative to the attached polymer branches. Comb polymers offer the advantage of increased wear.

There are numerous ways to prepare comb polymers. The most common involve the copolymerization of a polymerizable oligomer or polymer (i.e., macromonomer) with other monomers to generate the desired comb structure, as described in U.S. Pat. No. 3,390,206. Other approaches involve preparing a polymer backbone-bearing functionality that the polymer branches either grow from or are attached to in a subsequent step, as described in "Synthesis of Polymer Brushes Using Atom Transfer Radical Polymerization" Pyun, J., Kowalewski, T., Matyjaszewki, T. *Macromolecular Rapid Communications* 2003, 24(18), 1043-1059. In either case, the formed comb polymer can optionally be joined to another polymer backbone to form a new comb polymer with more complex branching structure.

In some embodiments, the branched polymers may include one or more reactive groups in the polymer chain. For example, the polymer chain may include at least 0.5 moles or at least 1.0 moles of reactive double bonds per polymer molecule. In some embodiments, the polymer chain may include less than 2.0 moles of reactive double bonds per molecule of polymer.

The adhesive may be applied to an uncoated (i.e. bare) nail surface to permit removal of subsequent coverings from the adhesive-coated nail surface. Alternatively, the adhesive may be applied to a coated nail surface, e.g., a nail surface coated with a base coat or color coat.

A number of different nail coverings may be applied to the adhesive-coated nail surface. In some embodiments, an evaporative nail polish may be applied to the adhesive-coated surface. Such polishes form a film when the solvent evaporates. The evaporative nail polishes may be solvent or water-based. Reactive nail polishes are also useful as nail coverings. Such polishes include reactive monomers that polymerize, e.g., by exposure to heat following application. Examples of suitable reactive nail polishes are commercially available and include, e.g., Orly Epix Nail Polish (Los Angeles, Calif.). Artificial nails or nail extensions may also be applied to the adhesive-coated surface. Commercially available examples include H&C Nail Extensions (Korea). Nail art may be used as well.

The adhesive-coated surfaces are particularly useful with curable nail gel coverings, e.g., base coats, color coats, and top coats, because such coverings are typically difficult to remove. Examples of suitable curable nail gels are described in U.S. Pat. No. 8,697,619, which is hereby incorporated by reference in its entirety.

Examples

Adhesive Synthesis

The following procedure describes the preparation of a representative crosslinked (meth)acrylate adhesive (butyl acrylate/butyl methacrylate/1,3 butylene glycol dimethacrylate).

To a 500 mL resin flask equipped with a condenser, nitrogen inlet, mechanical stirrer with a Teflon half-moon blade, and a heating mantle was added 170.7 g methyl ethyl ketone. The equipment was placed under a gentle flow of nitrogen, water started through the condenser, and agitation was started at 225 rpm. The solvent was then heated to 78-79° C. and held. To the hot solvent was added a solution of 55.0 g butyl acrylate, 40.0 g butyl methacrylate, 5.0 g 1,3-butylene glycol dimethacrylate, 1.0 g VAZO 52 (2,2'-azobis(2,4-dimethylvaleronitrile), and 10.0 g methyl ethyl ketone over 2 h. The temperature of the reaction solution was allowed to rise to 80-82° C. during the addition. After the addition was complete, the reaction solution was held at 80-82° C. for 30 min. A solution of 0.5 g VAZO 52 and 5.0 g methyl ethyl ketone was then added to the hot reaction solution in a single portion. The reaction solution was then held at 80-82° C. for 40 min after which it was cooled to not more than 35° C. and packaged.

Adhesive Peel Test

Adhesive peel strength was evaluated using the following test method.

On a 8 15/16 inch×5 14/16 inch×1/4 inch clean glass plate, three thin strips of each adhesive sample were placed approximately 1.5 inches apart. A 1.5 ml adhesive solution was used for each sample. Using an applicator brush, each sample was gently brushed out to fill an approximately 1 inch×3 inch area, after which solvent was allowed to evaporate for 5 minutes.

Each dried adhesive strip was coated with gel nail polish, leaving a 0.25 inch border beyond the adhesive border along the sides and bottom, and a 0.5 inch border beyond the top. Metal hooks were placed on the top border and pressed gently to submerge them into gel coating. The hooks were thin pieces of metal about 2 inch×1 inch bent to approximately 90° perpendicular to the main axis. Each hook had a small hole centered toward the top. 2 mL gel polish was placed on the surface of each hook or until they are completely sealed into the gel. The gel polish was cured by exposure to ultraviolet light for 3 minutes.

A fishing scale was secured to a three finger clamp, which in turn was secured to a ring stand such that the scale's hook was positioned one foot above the surface of the bench. The cured film directly underneath the metal hooks was gently loosened, by prying. The entire sample system (glass plate, hooks, etc.) was then placed on a lab jack and secured to the jack platform using binder clips. The lab jack platform was raised until the scale could be connected to a metal hook and positioned so the scale was being initially pulled directly downward. The lab jack was then lowered about 3.5 inches over about 10-15 seconds at a constant rate while observing the scale readout. The maximum readout of the fishing scale was recorded during this process. The process was then repeated for the other two strips and the mean of the three trials reported.

The peel force to remove the cured gel polish was measured for a number of different adhesives. The results are shown in Table 1.

TABLE 1

| Example | Composition | Peel Force (kg) |
|---|---|---|
| 1 | 58.2 BA/30.9 BMA/8.4 BGDMA/2.5 NVP | 3.01 |
| 2 | 56.5 BA/30 BMA/8.4 BGDMA/5 NVP | 3.24 |
| 3 | 58.2 BA/30.9 BMA/8.4 BGDMA/2.5 HEA | 2.76 |
| 4 | 56.5 BA/30 BMA/8.4 BGDMA/5 HEA | 3.85 |
| 5 | 58.2 BA/30.9 BMA/8.4 BGDMA/2.5 AA | 2.77 |
| 6 | 56.5 BA/30 BMA/8.4 BGDMA/5 AA | 3.12 |
| 7 | 69.2 BA/22.4 MMA/8.4 BGDMA | 2.49 |
| 8 | 59.8 BA/10.0 MMA/8.4 BGDMA | 1.58 |
| 9 | 81.6 BA/31.8 BMA/8.4 BGDMA | 1.24 |
| 10 | 72.3 BA/19.3 MA/8.4 BGDMA | 1.35 |
| 11 | 69 BA/20 BMA/11 BGDMA | 2.30 |
| 12 | 59.8 BA/31.8 BMA/8.4 BGDMA | 2.83 |
| 13 | 68.3 BA/26.6 BMA/5 BGDMA | 0.56 |
| 14 | 55 BA/40 BMA/5 BGDMA | 2.49 |
| 15 | 69 BA/20 BMA/11 BGDMA | 1.69 |
| 16 | 50 BA/39 BMA/11 BGDMA | 0.87 |
| 17 | 75 BA/20 BMA/5 BGDMA | 0.73 |
| 18 | 95 BA/4 BMA/1 BGDMA | 0.28 |
| 19 | 89.25 BA/10 BMA/0.75 BGDMA | 0.32 |
| 20 | 97 BA/2.15 BMA/0.875 BGDMA | 0.27 |
| 21 | 88.75 BA/10 BMA/1.25 BGDMA | 0.29 |
| 22 | 92.1 BA/7.025 BMA/0.8751 BGDMA | 0.26 |
| 23 | 88.75 BA/10 BMA/1.25 BGDMA | 0.21 |
| 24 | 98.75 BA/0 BMA/1.25 BGDMA | 0.25 |
| 25 | 53.5 BA/44 LMA/2.5 ALMA | 0.53 |
| 26 | 88.2 BA/10 LMA/1.83 ALMA | 0.32 |
| 27 | 62.75 BA/35.5 LMA/1.75 ALMA | 0.82 |
| 28 | 76.2 BA/21.3 LMA/2.5 ALMA | 0.24 |
| 29 | 71 BA/27 LMA/2 ALMA | 0.34 |
| 30 | 54.5 BA/44 LMA/1.5 ALMA | 0.91 |
| 31 | 88.2 BA/10 LMA/1.83 ALMA | 0.28 |
| 32 | 37.5 BA/42.9 LMA/0.616 AA/1.5 ALMA/17.4 BMA | 0.26 |
| 33 | 22.5 BA/25 LMA/0 AA/1.5 ALMA/51 BMA | 0.87 |
| 34 | 22.5 BA/25 LMA/1 AA/0.5 ALMA/51 BMA | 0.69 |
| 35 | 22.5 BA/25 LMA/0 AA/1.5 ALMA/51 BMA | 0.62 |
| 36 | 22.5 BA/75 LMA/1 AA/1.5 ALMA | 0.13 |
| 37 | 50 BA/49.5 LMA/0 AA/0.5 ALMA | 0.16 |
| 38 | 22.5 BA/75 LMA/1 AA/1.5 ALMA | 0.25 |
| 39 | 22.5 BA/59.8 LMA/0 AA/0.5 ALMA/17.2 BMA | 0.07 |
| 40 | 50 BA/49.5 LMA/0 AA/0.5 ALMA | 0.08 |
| 41 | 50 BA/25 LMA/1 AA/1.5 ALMA/22.5 BMA | 0.26 |
| 42 | 22.5 BA/41.0 LMA/1 AA/1 ALMA/34.5 BMA | 0.70 |
| 43 | polyvinylacetate copolymer in water[1] | 0.20 |
| 44 | Styrene-(Meth)acrylate copolymer[2] | 0.57 |
| 45 | Styrene-Butadiene (SBR) copolymer[3] | 1.60 |
| 46 | (Meth)acrylate-Butadiene-Styrene (MBS) copolymer[4] | 3.33 |
| 47 | natural rubber (polyisoprene)[5] | 0.74 |
| 48 | Polydimethylsiloxane polymer[6] | 0.50 |
| 49 | Copal resin[7] | 0.28 |
| 50 | 55.0 BA/40.0 BMA/5.0 BGDMA[8] | 8.71 |

[1]Elmer's Glue (Elmer's Products, OH)
[2]Aleene's Fabric Fusion (iLoveToCreate, CA)
[3]Shoe Goo (Eclectic Products, LA)
[4]Spray Bond (Elmer's Products, OH)
[5]Rubber Cement (Elmer's Products, OH)
[6]DAP Sealant (DAP, MD)
[7]Spirit Gum (Spirit Halloween, NJ)
[8]Polymerized in situ on glass surface.
BA = Butyl Acrylate
LMA = Lauryl Methacrylate
BMA = Butyl Methacrylate
AA = Acrylic Acid
ALMA = Allyl Methacrylate
BGDMA = Butylene Glycol Dimethacrylate
HEA = Hydroxyethyl acrylate
NVP = N-vinyl pyrollidone.

The following examples describes the preparation of a representative comb polymer adhesive.

To a round-bottomed flask equipped with an overhead stirrer, thermocouple and nitrogen sparge was charged 137.3 g Ethyl Acetate (EA) and 22.8 g Methyl Ethyl Ketone (MEK) making a solvent solution in a reaction flask. Stirring was started and the resulting solvent solution was heated to 78° C. In a second vessel, a monomer mix solution was made consisting of 47.5 g Butyl Acrylate (BA), 34.6 g Butyl Methacrylate (BMA), and 4.32 g 1,3-Butylene Glycol Dimethacrylate. In a third vessel, an initiator solution was made consisting of 0.48 g Vazo 52 (Chemours) dissolved in 27.45 g of a polyacrylate solution consisting of a ~10K MW methacrylate terminated polyacrylate copolymer with a hydroxyl number of 335 dissolved in 59.1 parts MEK and 13.9 parts EA. Both the monomer solution and the initiator solution were simultaneously added to the reaction flask over two hours with gentle stirring maintaining a temperature of 78-82° C. The addition was exothermic.

After the feeds were completed, the reaction mass was maintained at 80-82° C. for an additional 20 min before adding an initiator solution consisting 0.48 g Vazo 52 in 2.00 g MEK. The reaction contents were held at 80-82° C. for an additional 40 min before heating and distilling away 132 g of solvent. The reaction mixture was allowed to cool to 80-82° C. and an additional initiator solution consisting of 0.48 g Vazo 52 in 2.00 g MEK was added. The reaction mixture was maintained at 80-82° C. for 45 min before cooling to 70° C. A solution consisting of 0.0012 g 4-Hydroxy-(2,2,6,6-Tetramethylpiperidin-1-Y1)Oxyl (4-Hydroxy-TEMPO) dissolved in 0.38 g Glycidyl Methacrylate and 1.3 g of a 1% solution of Aluminum Triflate in MEK was added to the reaction mass. The reaction mass was maintained at 70° C. for 3 h before adding a monomer mixture consisting of 58.4 g BMA and 25.0 g BA. The temperature was adjusted to 73° C. before adding an initiator solution consisting of 0.42 g Vazo 52 in 3 g EA. The reaction temperature was allowed to rise to 81-84° C. and was held for 45 min at 81-84° C. An initiator solution consisting of 0.42 g Vazo 52 in 3.00 g EA was added and the reaction mixture was maintained at 80-82° C. for 45 min. An additional initiator solution consisting of 0.42 g Vazo 52 dissolved in 3.00 g EA was added again maintaining the reaction contents at 80-82° C. for 45 minutes. The reaction mass was diluted with 365 g EA and mixed for 30 min before packing out.

The wear properties of the above-described comb polymer adhesive were evaluated as follows.

The nails of twelve women were lightly buffed and then dried (with an isopropyl alcohol swab) before applying the comb polymer adhesive. The adhesive was allowed to dry momentarily and various colors of nail gel (Keystone Gel Polish Color) were applied and cured for 30 sec under a UV LED lamp. The color coat was reapplied and similarly cured. A clear top coat (Keystone Gel Polish Top) was applied and cured and the tacky layer was removed with an isopropanol wetted nail wipe.

The nails were monitored for wear over time. The wear test was concluded at the first sign of unacceptable coating lifting. After the conclusion of the wear test, the nail coatings were peeled and any removal difficulty or nail damage was recorded. The median average wear was 6.5 days for the group with a high of nine days. All respondents encountered acceptable ease of removal and no nail damage. Removal was judged acceptable if the respondent could remove the nail coating by hand with the application of minimal force (<~1.5 kg/in). Nail damage was determined visually by examining the nail for surface defects present after coating and any adhesive residue removed.

The following example describes the preparation of a lightly functionalized polymer having reactive groups.

A monomer solution consisting of 55.0 g butyl acrylate, 40.0 g butyl methacrylate, and 0.5 g 3-mercaptoproprionic acid, and a catalyst solution consisting of 0.5 g Vazo-52 (Chemours Co.) dissolved in 10.0 g methyl ethyl ketone (MEK) was gradually added over 2 h to a stirred, nitrogen inerted solution of 51.0 g MEK at 79° C. During the feeds, the temperature was allowed to rise to 82-84° C. At the end of the feeds, the mixture was held at temperature for an additional 30 min. A solution of 0.5 g Vazo-52 dissolved in 5 g MEK was added rapidly to the reaction mixture, which was then held an additional 45 min at 80-82° C. The batch was heated to 88° C. and held 30 min. A solution consisting of 0.0008 g 4-hydroxy-(2,2,6,6-tetramethyl-piperidin-1-yl) oxyl dissolved in 0.67 g glycidyl methacrylate was added along with 0.47 g triethylamine. The reaction mixture was held at 88° C. for 6 h. The batch was then cooled and packed out.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating a nail surface comprising:
    (a) brushing or spraying a prepolymerized, non-aqueous solvent-based adhesive on an uncoated nail surface, upon drying the adhesive forming a tacky surface to which a covering may be adhered; and
    (b) applying a covering to the adhesive-coated tacky surface, wherein the covering is an evaporative nail polish or a curable gel coating selected from the group consisting of base coats, color coats, and top coats, wherein following application the covering is removable by peeling.

2. The method of claim 1 wherein the adhesive is applied to the entire nail surface.

3. The method of claim 1 wherein the adhesive is applied to a portion of the nail surface.

4. The method of claim 1 wherein the adhesive is selected from the group consisting of (meth)acrylates, silicones, polyvinyl acetates, polyethylene vinyl acetates, polyisoprene rubbers, styrene-methacrylate copolymers, styrene-butadiene rubbers, methacrylatebutadiene-styrene copolymers, and combinations thereof.

5. The method of claim 1 wherein the adhesive comprises a crosslinked (meth)acrylate copolymer.

6. The method of claim 5 wherein the adhesive is the polymerization product of (a) a C1-C20 alkyl methacrylate monomer; (b) a C1-C20 alkyl acrylate monomer; and (c) an ethylenically unsaturated (meth)acrylate crosslinking monomer.

7. The method of claim 6 wherein the alkyl methacrylate monomer is butyl methacrylate, the alkyl acrylate monomer is butyl acrylate, and the crosslinking monomer is an alkylene glycol dimethacrylate.

8. The method of claim 1 wherein the adhesive comprises a comb polymer.

9. The method of claim 1 wherein the adhesive comprises a polymer having one or more reactive functional groups.

10. A method for treating a nail surface comprising:
    (a) brushing or spraying a prepolymerized, non-aqueous solvent-based adhesive on an uncoated nail surface, upon drying the adhesive forming a tacky surface to which a covering may be adhered; and (b) applying a covering to the adhesive-coated tacky surface, wherein the covering is an evaporative nail polish or a curable gel coating selected from the group consisting of base coats, color coats, and top coats, wherein following application the covering is removable by soaking in a solvent for less than 20 minutes, peeling, or a combination thereof, and wherein the adhesive comprises a crosslinked (meth) acrylate copolymer.

11. The method of claim 10 wherein the adhesive is applied to the entire nail surface.

12. The method of claim 10 wherein the adhesive is applied to a portion of the nail surface.

13. The method of claim 10 wherein the covering is removable after soaking in a solvent for less than 20 minutes.

14. The method of claim 13 wherein the covering is removable after soaking in a solvent for less than 10 minutes.

15. The method of claim 10 wherein the covering is removable by peeling.

16. The method of claim 15 wherein at least a portion of the adhesive is configured to remain on the nail surface after the covering is removed by peeling.

17. The method of claim 10 wherein the adhesive is the polymerization product of (a) a C1-C20 alkyl methacrylate monomer; (b) a C1-C20 alkyl acrylate monomer; and (c) an ethylenically unsaturated (meth)acrylate crosslinking monomer.

18. The method of claim 17 wherein the alkyl methacrylate monomer is butyl methacrylate, the alkyl acrylate monomer is butyl acrylate, and the crosslinking monomer is an alkylene glycol dimethacrylate.

19. The method of claim 10 wherein the adhesive comprises a comb polymer.

20. The method of claim 10 wherein the adhesive comprises a polymer having one or more reactive functional groups.

* * * * *